(12) United States Patent
Pan et al.

(10) Patent No.: US 9,394,575 B2
(45) Date of Patent: Jul. 19, 2016

(54) PROBIOTIC COMPOSITION CONTAINING LACTOBACILLUS PARACASEI SUBSP. PARACASEI NTU 101 FOR AMELIORATING INTESTINAL FLORA AND REDUCING GASTRIC MUCOSAL LESION INDEX AND HISTAMINE CONCENTRATION IN GASTRIC MUCOSAL

(71) Applicant: Sunway Biotech Co., LTD, Taipei (TW)

(72) Inventors: Tzu-Ming Pan, Taipei (TW); Chih-Hui Lin, Taipei (TW); Tsung-Wei Shih, Taipei (TW)

(73) Assignee: SUNWAY BIOTECH CO., LTD. (TW)

( * ) Notice: Subject to any disclaimer, the term of this patent is extended or adjusted under 35 U.S.C. 154(b) by 0 days.

(21) Appl. No.: 14/551,458

(22) Filed: Nov. 24, 2014

(65) Prior Publication Data

US 2015/0152487 A1    Jun. 4, 2015

(30) Foreign Application Priority Data

Nov. 29, 2013    (CN) .......................... 2013 1 0632681
Sep. 15, 2014    (CN) .......................... 2014 1 0468601

(51) Int. Cl.
| | |
|---|---|
| C12N 1/20 | (2006.01) |
| A61K 35/747 | (2015.01) |
| C12N 15/00 | (2006.01) |
| C12Q 1/68 | (2006.01) |
| C12R 1/225 | (2006.01) |
| A61K 35/00 | (2006.01) |

(52) U.S. Cl.
CPC .............. *C12Q 1/689* (2013.01); *A61K 35/747* (2013.01); *C12N 1/20* (2013.01); *C12R 1/225* (2013.01); *A61K 2035/115* (2013.01); *C12Q 2600/158* (2013.01)

(58) Field of Classification Search
CPC ............. C12N 1/20; C12N 15/52; C12P 7/56; C12R 1/225; A61K 2035/115; A61K 35/747; A61K 35/74; A23L 1/3014
USPC ................ 435/183, 252.3, 320.1, 252.5, 854; 424/93.45; 426/43
See application file for complete search history.

(56) References Cited

PUBLICATIONS

Morgan et al. J. Micriobiol Method 2006,66, pp. 183-193.*

* cited by examiner

*Primary Examiner* — MD. Younus Meah

(57) ABSTRACT

The present invention relates to a *lactobacillus* mutant, a nucleotide sequence for *lactobacillus* mutant, and primers for nucleotide sequence of *lactobacillus* mutant. The *lactobacillus* mutant is *Lactobacillus paracasei* subsp. *paracasei* NTU 101 having the nucleotide sequence of SEQ ID NO 1, and deposited with Deutsche Sammlung von Mikroorganismen and Zellkulturen GmbH (DSMZ, Germany) on Nov. 18, 2013, wherein the accession number of *Lactobacillus paracasei* subsp. *paracasei* NTU 101 is DSM 28047. Moreover, a nucleotide sequence for NTU 101 and the primers for the nucleotide sequence are also proposed for facilitating the person skilled in *Lactobacillus* filed capable of carrying out the strain identification of the NTU 101 according to the present invention. Moreover, the person skilled in *Lactobacillus* filed can also rapidly complete the strain identification of the NTU 101 by using DNA molecular marker technology, without culturing any isolated *Lactobacillus* strain or live *Lactobacillus* bacteria.

6 Claims, 12 Drawing Sheets

| Gastric Lesion | Image Analysis | Gastric Lesion | Image Analysis |
|---|---|---|---|
| C group | | | |
|  |  | | |
| 0.5X group | | Live group | |
|  |  |  |  |
| 1X group | | D-A group | |
|  |  |  |  |
| 5X group | | D-B group | |
|  |  |  |  |

PROBIOTIC COMPOSITION CONTAINING *LACTOBACILLUS PARACASEI* SUBSP. *PARACASEI* NTU 101 FOR AMELIORATING INTESTINAL FLORA AND REDUCING GASTRIC MUCOSAL LESION INDEX AND HISTAMINE CONCENTRATION IN GASTRIC MUCOSAL

SEQUENCE LISTING

The instant application contains a Sequence Listing which has been submitted in ASCII format via EFS-Web and is hereby incorporated by reference in its entirety. The ASCII copy is named sequence.txt and is 2,105 bytes in size.

BACKGROUND OF THE INVENTION

1. Field of the Invention

The present invention relates to a *lactobacillus* mutant, and more particularly to a *Lactobacillus paracasei* subsp. *paracasei* NTU 101, a nucleotide sequence for *Lactobacillus* NTU 101 and primers for nucleotide sequence of *Lactobacillus* NTU 101.

2. Description of the Prior Art

Lactate bacteria is one kind of bacteria able to metabolize carbohydrate and then produce over 50% lactic acid; for example, *Lactobacillus, Streptococcus* and *Leuconostoc*. Because the fermented milk products are traditional and historical drinks for human, the lactate bacteria is regarded as a safe bacteria and a representative intestinal probiotics. Moreover, the lactate bacteria is one of the important probiotics, which is able to enhance the quality of intestinal flora through the following ways:

(1) producing organic acids and reducing intestinal pH value;
(2) absorbing nutrients by way of competing with pernicious bacteria;
(3) adhering to intestinal epithelium for reducing the growth sites of pernicious bacteria; and
(4) producing antibiotic substances.

Nowadays, a variety of fermented milk products have been proven their ability of increasing the intestinal probiotics after the related human experimentation is completed. *Lactobacillus paracasei* subsp. *paracasei* NTU 101 is an excellent local *Lactobacillus* strain, and which is studied and developed by Tzu-Ming PAN, the graduate chair of Institute of Microbiology and Biochemistry of National Taiwan University, and the R&D team thereof. Besides, currently, the health-care characteristics of improving the quality of intestinal flora, decreasing the blood pressure, the hyperlipidemia and the cholesterol, and anti-allergy of the *Lactobacillus paracasei* subsp. *paracasei* NTU 101 as well as the its related fermented products have been proven, and the *L. paracasei* subsp. *paracasei* NTU 101 is successful to be commercialized. However, in spite of that, the strain (mutant) identification and the DNA molecular marker of the *L. paracasei* subsp. *paracasei* NTU 101 does still not be carried out, wherein the DNA molecular marker technology is usually used for identifying the DNA sequence or the RAPD genetic variation map.

Accordingly, in view of the specific DNA sequence, the specific RAPD genetic variation map, and the DNA molecular marker of the *L. paracasei* subsp. *paracasei* NTU 101 still does not be finished, the inventor of the present application has made great efforts to make inventive research thereon and eventually provided a *Lactobacillus* mutant, a nucleotide sequence for *Lactobacillus* mutant and primers for nucleotide sequence of *Lactobacillus* mutant.

SUMMARY OF THE INVENTION

The primary objective of the present invention is to provide a *Lactobacillus paracasei* subsp. *paracasei* NTU 101, a nucleotide sequence for *Lactobacillus* NTU 101 and primers for nucleotide sequence of *Lactobacillus* NTU 101, therefore the person skilled in *Lactobacillus* filed is able to carried out the strain (mutant) identification of the *Lactobacillus paracasei* subsp. *paracasei* NTU 101 according to the present invention. Moreover, the person skilled in *Lactobacillus* filed can also rapidly complete the strain (mutant) identification of the *Lactobacillus* NTU 101 by using DNA molecular marker technology, without culturing any isolated *Lactobacillus* strain or live *Lactobacillus* bacteria.

Accordingly, to achieve the primary objective of the present invention, the inventor of the present invention provides a *Lactobacillus* mutant, which is *Lactobacillus paracasei* subsp. *paracasei* NTU 101 having a nucleotide sequence of SEQ ID NO 1, and deposited with Deutsche Sammlung von Mikroorganismen und Zellkulturen GmbH (DSMZ, Inhoffenstr. 7B, D-38124 Braunschweig, Germany) in Nov. 18, 2013, wherein the accession number of the *Lactobacillus paracasei* subsp. *paracasei* NTU 101 is DSM 28047. Moreover, the nucleotide sequence of the *Lactobacillus paracasei* subsp. *paracasei* NTU 101 can be formed by treating the RAPD (Random Amplification of Polymorphic DNA) and the PCR (Polymerase Chain Reaction) process to a plurality of specific primers, wherein the specific primers comprising a first nucleotide sequence of SEQ ID NO 2 and a second nucleotide sequence of SEQ ID NO 3.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
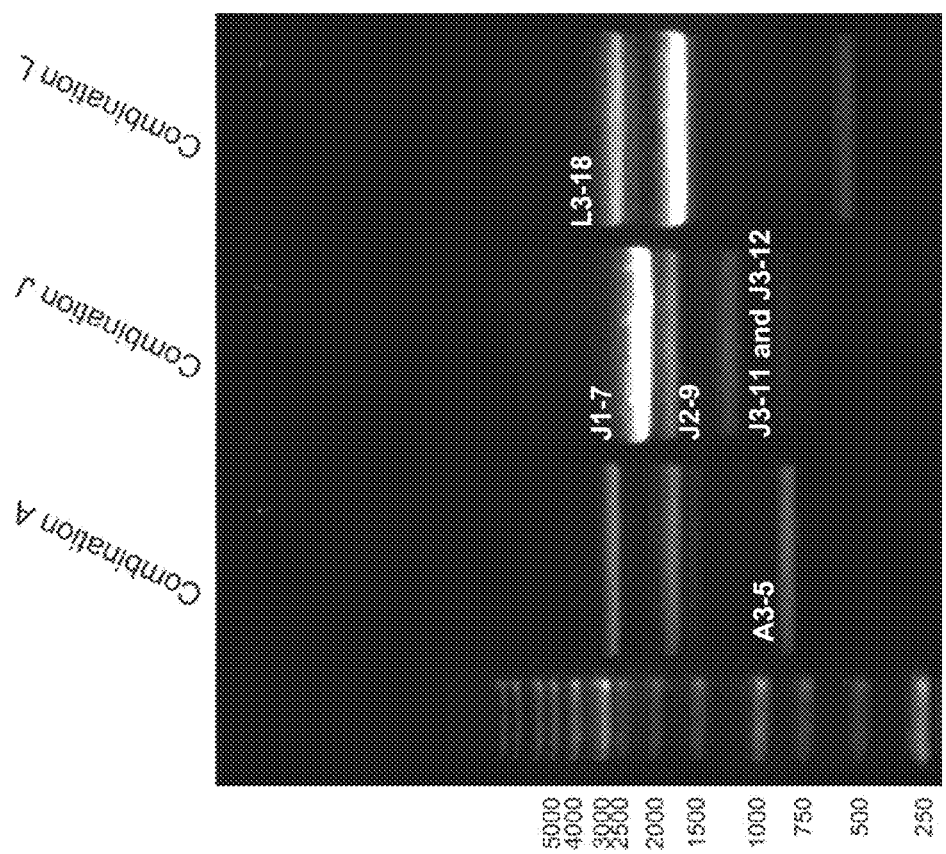
FIG. 1 is an image diagram of a RAPD genetic variation map of the primer compounds of A, J and L.

To more clearly describe a *Lactobacillus* Mutant, Nucleotide Sequences for the *Lactobacillus* Mutant and Primers for the Nucleotide Sequence of the *Lactobacillus* Mutant according to the present invention, embodiments of the present invention will be described in detail with reference to the attached drawings hereinafter.

NTU 101 *Lactobacillus* mutant is an excellent local *lactobacillus* strain, and which is studied and developed by Tzu-Ming PAN, the graduate chair of Institute of Microbiology and Biochemistry of National Taiwan University, and the R&D team thereof. In the present invention, the *Lactobacillus paracasei* subsp. *paracasei* NTU 101 having a specific nucleotide sequence of SEQ ID NO 1 was deposited with Deutsche Sammlung von Mikroorganismen und Zellkulturen GmbH (DSMZ, Inhoffenstr. 7B, D-38124 Braunschweig, Germany) on Nov. 13, 2009, and was given accession number DSM 28047

The *Lactobacillus paracasei* subsp. *paracasei* NTU 101 includes the characteristics of: gram-positive, lacking catalase, having the ability of curding, acid resistance ability, alkaline resistance ability, bile salt resistance ability, facultative heterogeneous fermentation, producing L(+)-lactate, having excellent ability of immune regulation. The basic culture medium for *Lactobacillus paracasei* subsp. *paracasei* NTU 101 is MRS medium, wherein the best culture temperature is 30° C., the best culture time is 24 hours, the best culture pH value is 6.5, the best culture pressure is 1 atm; moreover, the *Lactobacillus paracasei* subsp. *paracasei* NTU 101 needs microaerophilic growth.

Moreover, please refer to following table 1, which records and lists the amount of lactic acid produced by the *Lactobacillus paracasei* subsp. *paracasei* NTU 101 cultured in an identical culture medium containing different carbon sources, wherein the carbon sources are Glucose, Galactose, D-ribose, Xylose, Fructose, α-Lactose, Maltose, Sucrose, Trehalose, Raffinose, myo-Inositol, Sorbitol, D-mannitol, Citric acid, Dextrin, Starch, and Molasses, respectively.

TABLE 1

| Carbon source | viable count (Log CFU/mL) | pH value | Production amount of lactic acid (g/L) |
|---|---|---|---|
| Glucose | 9.43 | 3.73 | 17.48 |
| Galactose | 9.33 | 3.70 | 11.33 |
| D-ribose | 9.54 | 4.07 | 7.25 |
| Xylose | 8.94 | 6.37 | 0.40 |
| Fructose | 8.20 | 3.75 | 14.00 |
| α-Lactose | 9.26 | 3.87 | 11.64 |
| Maltose | 9.45 | 4.16 | 8.55 |
| Sucrose | 9.01 | 3.78 | 13.90 |
| Trehalose | 9.04 | 3.79 | 13.26 |
| Raffinose | 8.78 | 5.23 | 1.80 |
| myo-Inositol | 8.89 | 6.48 | 0.41 |
| Sorbitol | 9.65 | 4.15 | 7.49 |
| D-mannitol | 9.44 | 3.81 | 16.21 |
| Citric acid | 7.05 | 6.41 | 0.28 |
| Dextrin | 9.38 | 5.35 | 0.86 |
| Strach | 9.24 | 5.82 | 0.30 |
| Molasses | 9.70 | 4.50 | 6.02 |

Besides, please refer to following table 2, which records and lists the amount of lactic acid produced by the *Lactobacillus paracasei* subsp. *paracasei* NTU 101 cultured in an identical culture medium containing different nitrogen sources, wherein the nitrogen sources are Yeast extract, Beef extract, Peptone, Soytone, Tryptose, Corn-steep liquor, Casein, Urea, Ammonium citrate, and Ammonium sulfate, respectively. Therefore, through the listed data of the tables 1 and 2, the lactate-producing ability of the *Lactobacillus paracasei* subsp. *paracasei* NTU 101 of the present invention has been proven.

TABLE 2

| Nitrogen source | viable count (Log CFU/mL) | pH value | Production amount of lactic acid (g/L) |
|---|---|---|---|
| Yeast extract | 8.14 | 3.54 | 8.29 |
| Beef extract | 8.89 | 4.22 | 2.74 |
| Peptone | 8.95 | 3.74 | 5.91 |
| Soytone | 8.30 | 3.90 | 5.82 |
| Tryptose | 8.84 | 3.87 | 4.45 |
| Corn-steep liquor | 9.14 | 4.14 | 4.11 |
| Casein | 8.27 | 4.68 | 1.77 |
| Urea | 6.89 | 5.96 | 0.02 |
| Ammonium citrate | 7.09 | 6.04 | 0.08 |
| Ammonium sulfate | 6.69 | 5.84 | 0.07 |

Next, in order to identify the nucleotide sequence of the *Lactobacillus paracasei* subsp. *paracasei* NTU 101, 20 random primers are purchased from MDBio, Inc., located in Taipei of ROC, and the related information of the 20 random primers are listed in following table 3. Therefore, the 20 random primers are re-dissolved to 100 μM by using a sterile water, and stored in a 20° C. environment. In which, 20 random primers of B01, B02, B03, B04, B05, B06, B07, B08, B09, B10, D11, D12, D13, D14, D15, D16, D17, D18, D19, D20 are respectively identified as SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, and SEQ ID NO 26.

TABLE 3

| Primer ID | Primer Sequence (5'→3') |
|---|---|
| B01 | GTTTCGCTCC |
| B02 | TGATCCCTGG |
| B03 | CATCCCCCTG |
| B04 | GGACTGGAGT |
| B05 | TGCGCCCTTC |
| B06 | TGCTCTGCCC |
| B07 | GGTGACGCAG |
| B08 | GTCCACACGG |
| B09 | TGGGGGACTC |
| B10 | CTGCTGGGAC |
| D11 | AGCGCCATTG |
| D12 | CACCGTATCC |
| D13 | GGGGTGACGA |
| D14 | CTTCCCCAAG |
| D15 | CATCCGTGCT |
| D16 | AGGGCGTAAG |
| D17 | TTTCCCACGG |
| D18 | GAGAGCCAAC |
| D19 | CTGGGGACTT |
| D20 | ACCCGGTCAC |

Continuously, please refer to following table 4, which recorded and listed 16 primer compounds, wherein the 16 primer compounds are prepared by mixing the 20 random primers, and each of the 16 primer compounds have a final concentration of 1 μM. Furthermore, the 16 primer compounds would be amplified to form a probable nucleotide sequence of the *Lactobacillus paracasei* subsp. *paracasei* NTU 101 by way of being treated the RAPD (Random Amplification of Polymorphic DNA) and the PCR (Polymerase Chain Reaction) process.

TABLE 4

| primer compound | primers |
| --- | --- |
| A | B01, B02, D11, andD12 |
| B | B03, B04, D13, and D14 |
| C | B05, B06, D15, andD16 |
| D | B07, B08, D17, and D18 |
| E | B09, B10, D19, and D20 |
| F | B07, B08, B09, and D10 |
| G | D11, D12, D13, and D14 |
| H | D15, D16, D17, and D18 |
| I | B01, B02, D13, and D14 |
| J | B03, B04, D15, and D16 |
| K | B05, B06, D17, and D18 |
| L | B08, B09, D19, and D20 |
| M | B05, B06, D11, and D20 |
| N | B03, B04, D11, and D20 |
| O | B07, B08, D11, and D20 |
| P | B09, B10, D11, and D20 |

After the 16 primer compounds are prepared, the 16 primer compounds are next treated with a polymerase chain reaction (PCR) process. The polymerase chain reaction cocktail contains 3 ng DNA, 80 nM primers, a 1× Exsel reaction buffer, 5U Exsel DNA polymerase (Bertec Enterprise, Taipei, Taiwan), and 200 M dNTPs. The reaction conditions of the PCR is as described: 95° C. (5 min) for heating; 95° C. (30 sec) for heating; 25° C. (3 min) for adhesion and 70° C. (3 min) for extension (35 cycles); and 70° C. (7 min) for extension.

Moreover, after completing the PCR process, it is able to execute the electrophoresis analysis for the PCR products by using 1% agarose gel. Next, the agarose gels of the PCR products are dyed for 30 min by using the dying agent of SYBR Safe (Life Technologies Corporation). Eventually, after 20 min destain, the dyed agarose gels of the PCR products are disposed into a blue light (488 nm) box for observing and taking image picture by using an image process system. Furthermore, the dyed agarose gels are divided to a plurality of segments by using FavorPrep™ Gel/PCR Purification Kit (Favorgen biotech Corp), and then the cloning of the agarose gel segments are finished by using T&ATM Cloning Kit (Yeastern Biotech Co., Ltd., Taipei, Taiwan). Finally, the specific nucleotide sequence of the *Lactobacillus paracasei* subsp. *paracasei* NTU 101 is identified.

Please refer to FIG. 1, there is shown an image diagram of a RAPD genetic variation map of the primer compounds of A, J and L. In the 16 primer compounds listed in above table 4, as shown in FIG. 1, there are only the primer compounds of J and especially A and L can be amplified and form the RAPD genetic variation map revealing the specificity of *Lactobacillus paracasei* subsp. *paracasei* NTU 101. Next, in order to further confirm the specificity of *Lactobacillus paracasei* subsp. *paracasei* NTU 101, as shown in following table 5, there is a *Lactobacillus casei* group having the genetic relationship to the *L. paracasei* subsp. *paracasei*, and the *Lactobacillus casei* group including 12 *L. paracasei*, 10 *L. casei*, 7 *L. rhamnosus*, and 3 *L. zeae*. The *Lactobacillus* strains listed in table 5 are used for PCR specificity test. These strains are not directly related to the strains used in FIG. 4 and FIG. 5 except *L. paracasei* BCRC 12248T (=*L. paracasei* subsp. *paracasei* ATCC 25302) and *L. paracasei* subsp. *paracasei* BCRC 17002 (=*L. casei* ATCC 334).

TABLE 5

| Microorganism | ID/BCRC |
| --- | --- |
| Lactobacillus casei | BCRC 10358 |
| Lactobacillus casei | BCRC 10697T |
| Lactobacillus casei | BCRC 11197 |
| Lactobacillus casei | BCRC 12272 |
| Lactobacillus casei | BCRC 14025 |
| Lactobacillus casei | BCRC 16093 |
| Lactobacillus casei | BCRC 16094 |
| Lactobacillus casei | BCRC 17001 |
| Lactobacillus casei | BCRC 17004 |
| Lactobacillus casei | BCRC 17487 |
| Lactobacillus paracasei subsp. paracasei | BCRC 12188 |
| Lactobacillus paracasei subsp. paracasei | BCRC 12248T |
| Lactobacillus paracasei subsp. paracasei | BCRC 14001 |
| Lactobacillus paracasei subsp. paracasei | BCRC 14023 |
| Lactobacillus paracasei subsp. paracasei | BCRC 16100 |
| Lactobacillus paracasei subsp. paracasei | BCRC 17002 |
| Lactobacillus paracasei subsp. paracasei | BCRC 17483 |
| Lactobacillus paracasei subsp. paracasei | BCRC 17484 |
| Lactobacillus paracasei subsp. tolerans | BCRC 17485 |
| Lactobacillus paracasei subsp. paracasei | BCRC 17488 |
| Lactobacillus paracasei subsp. paracasei | BCRC 17489 |
| Lactobacillus paracasei | BCRC 80062 |
| Lactobacillus zeae | BCRC 17647T |
| Lactobacillus zeae | BCRC 17942T |
| Lactobacillus zeae | BCRC 80156 |
| Lactobacillus rhamnosus | BCRC 10940T |
| Lactobacillus rhamnosus | BCRC 11673 |
| Lactobacillus rhamnosus | BCRC 12249 |
| Lactobacillus rhamnosus | BCRC 14027 |
| Lactobacillus rhamnosus | BCRC 16095 |
| Lactobacillus rhamnosus | BCRC 17006 |
| Lactobacillus rhamnosus | BCRC 17007 |
| Lactobacillus rhamnosus | BCRC 80065 |

Figure 2A:
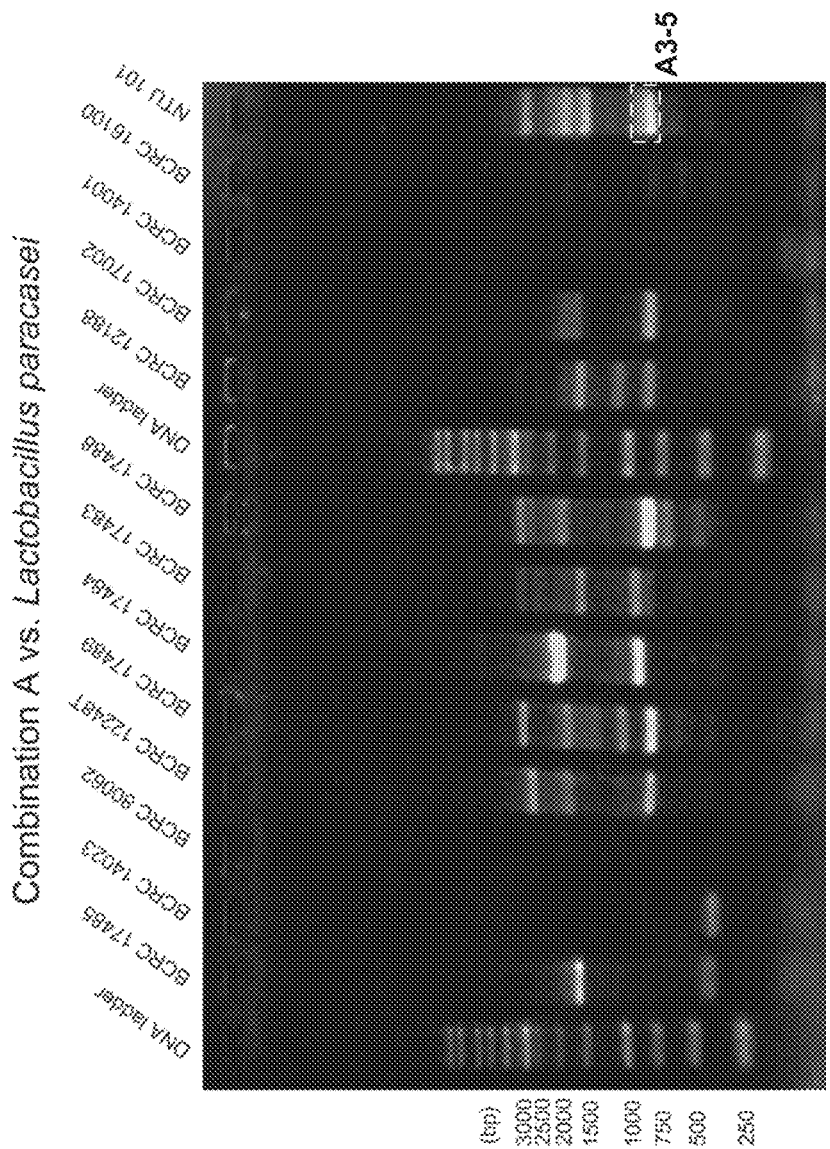
FIGS. 2A, 2B and 2C are shown comparing RAPD genetic variation maps of the primer compound A and *Lactobacillus casei* group.
Figure 2B:
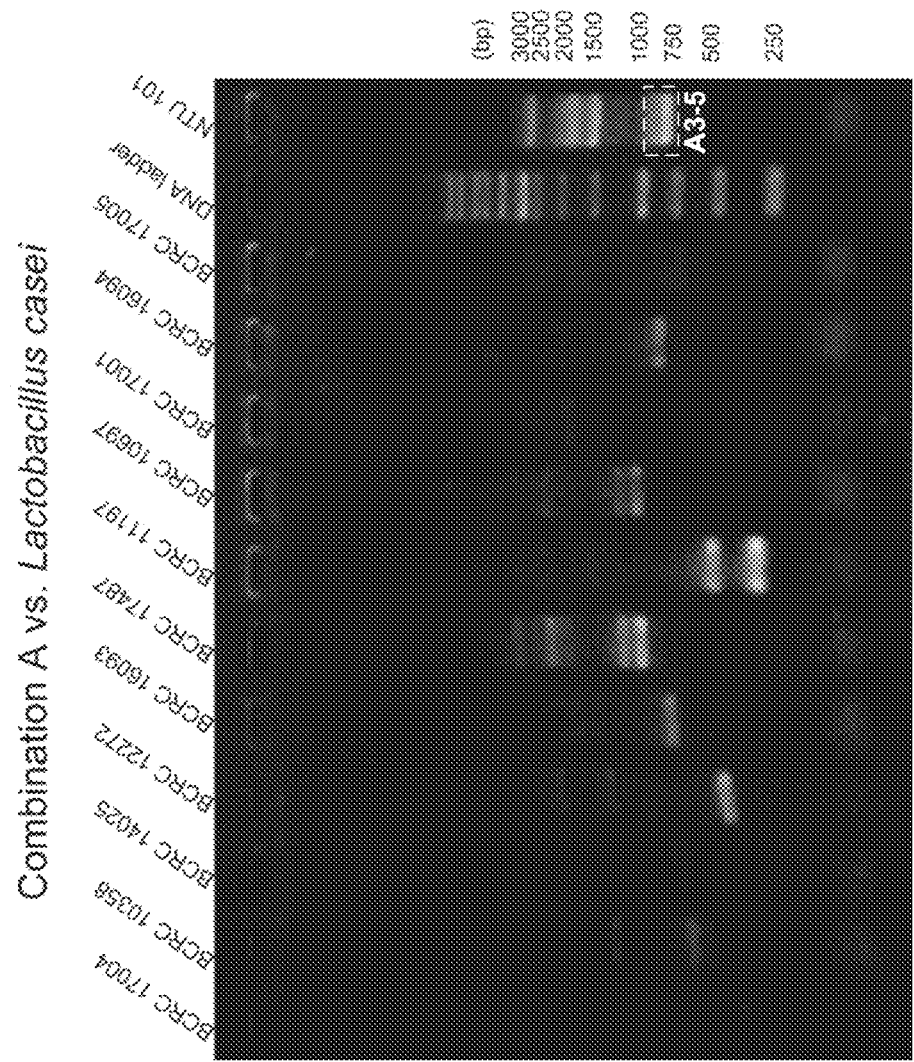
Figure 2C:
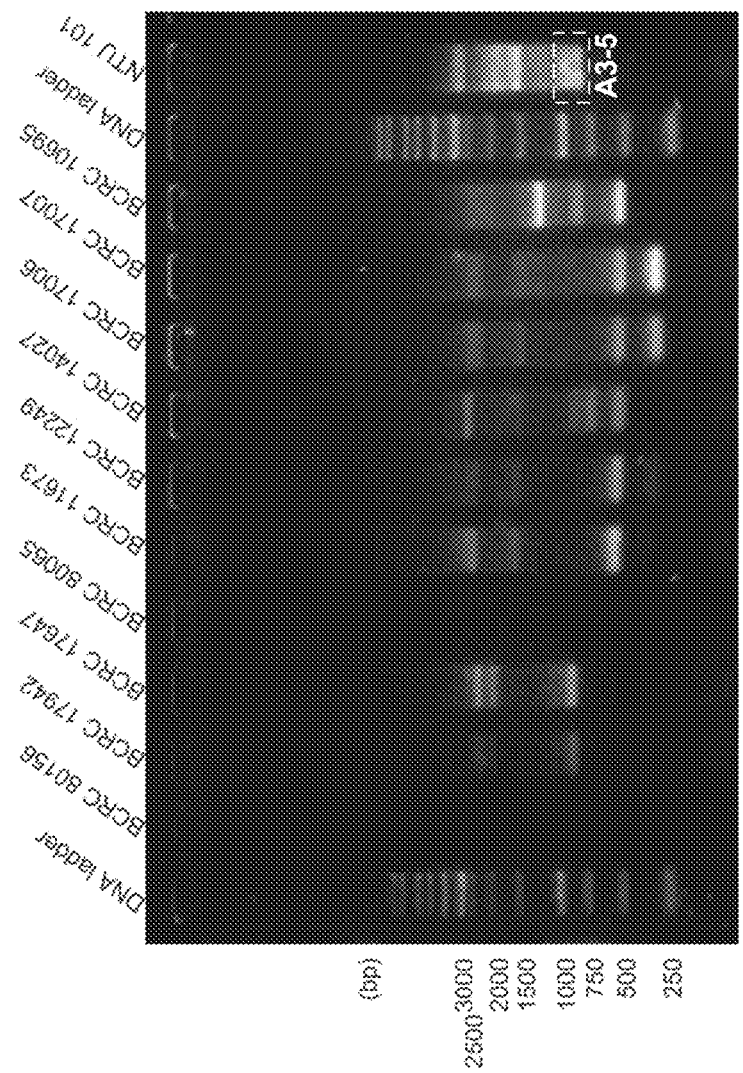

Please refer to FIGS. 2A, 2B and 2C, there are shown comparing RAPD genetic variation maps of the primer compound A and the *Lactobacillus casei* group. As shown in FIG. 2A, obviously, there has a large sequence difference between the (nucleotide) sequence of the RAPD genetic variation map of primer compound A and the sequence of the RAPD genetic variation map of the *Lactobacillus paracasei*. Besides, as shown in FIG. 2B, apparently, there has a large sequence difference between the (nucleotide) sequence of the RAPD genetic variation map of primer compound A and the sequence of the RAPD genetic variation map of the *Lactobacillus casei*. Moreover, as shown in FIG. 2C, distinctly, there has a large sequence difference between the (nucleotide) sequence of the RAPD genetic variation map of primer compound A and the sequence of the RAPD genetic variation map of the *Lactobacillus zeae* and the *Lactobacillus rhamnosus*. The distinctiveness of the RAPD genetic variation map of primer compound A is came from the primers B02 and D11, and this distinctive primer compound A is further marked as A3-5. Through the Sequence Listing, it is able to know that the nucleotide sequence of A3-5 is identified as SEQ ID NO 1 and includes the sequence length of 838 bp; besides, the nucleotide sequence of primer B02 is identified as SEQ ID NO 2 and includes the sequence length of 10 bp; moreover, the nucleotide sequence of primer D11 is identified as SEQ ID NO 3 and includes the sequence length of 10 bp.

Figure 3A:
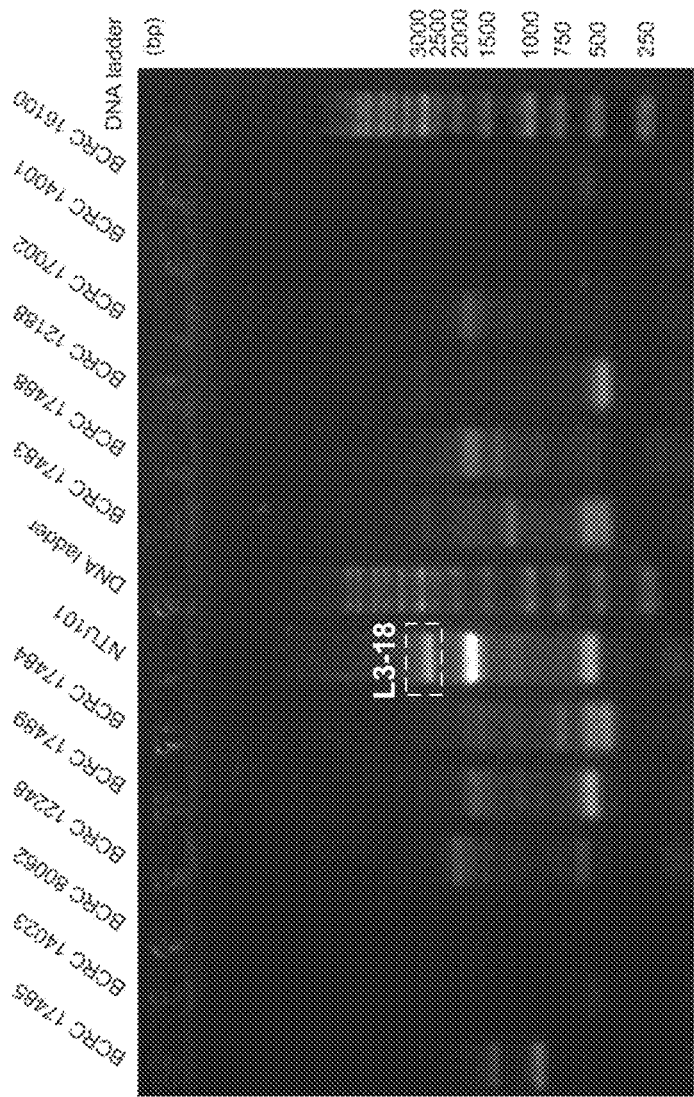
FIGS. 3A, 3B and 3C, are shown comparing RAPD genetic variation maps of the primer compound L and the *Lactobacillus casei* group.
Figure 3B:
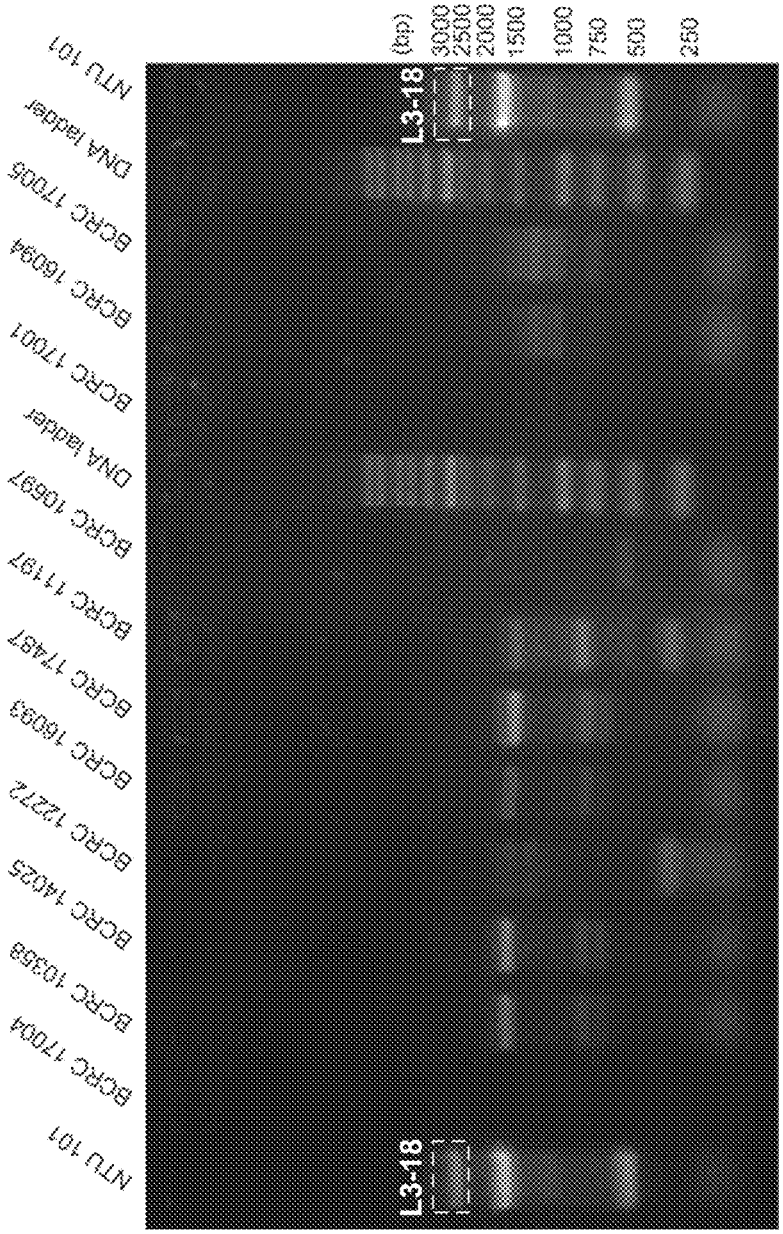
Figure 3C:
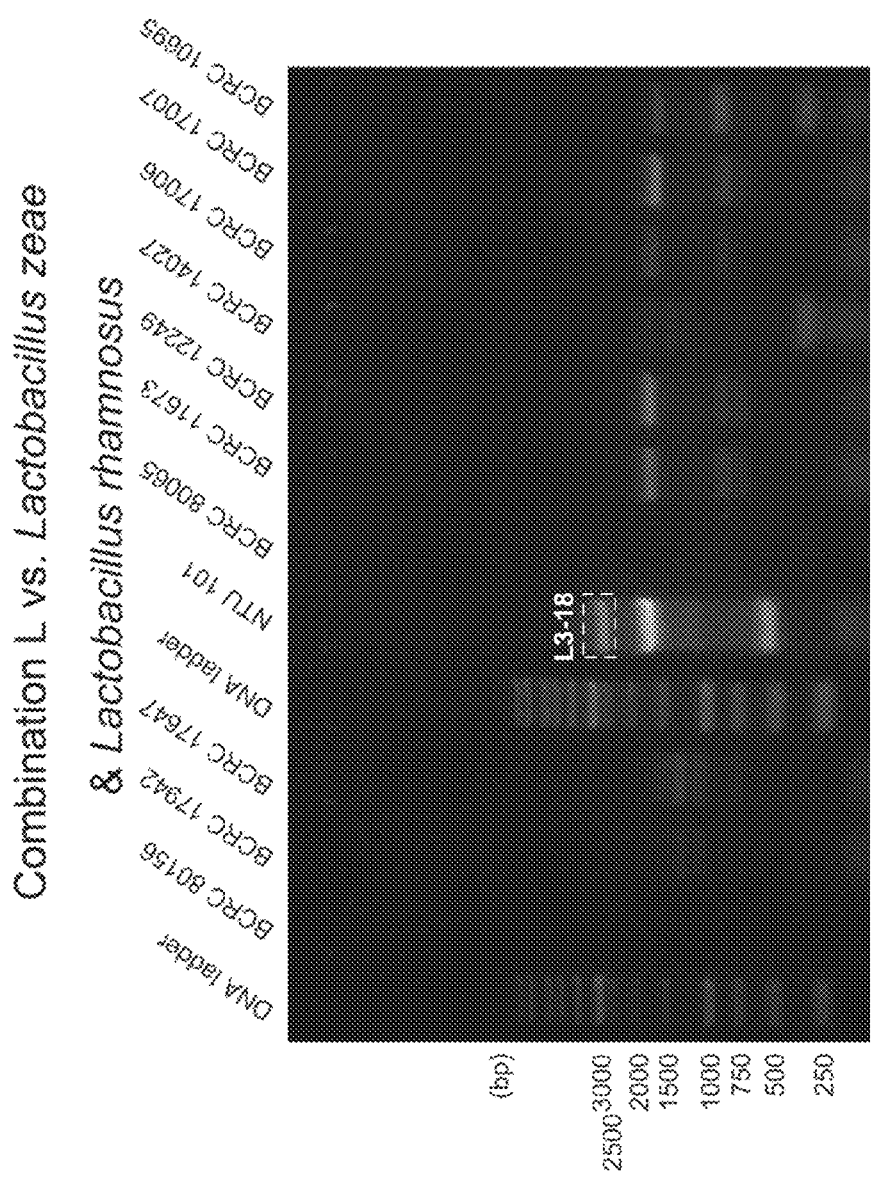

Continuously, please refer to FIGS. 3A, 3B and 3C, there are shown comparing RAPD genetic variation maps of the primer compound L and the *Lactobacillus casei* group. As shown in FIG. 3A, obviously, there has a large sequence difference between the (nucleotide) sequence of the RAPD genetic variation map of primer compound L and the sequence of the RAPD genetic variation map of the *Lactobacillus paracasei*. Besides, as shown in FIG. 3B, apparently, there has a large sequence difference between the (nucleotide) sequence of the RAPD genetic variation map of primer compound L and the sequence of the RAPD genetic variation map of the *Lactobacillus casei*. Moreover, as shown in FIG. 3C, distinctly, there has a large sequence difference between the (nucleotide) sequence of the RAPD genetic variation map of primer compound L and the sequence of the RAPD genetic variation map of the *Lactobacillus zeae* and the *Lactobacillus rhamnosus*. The distinctiveness of the RAPD genetic variation map of primer compound L is came from the primers B09 and D19, and this distinctive primer compound L is further marked as L3-18. According to following table 6, the nucleotide sequence of L3-18 includes the sequence length of 2477 bp, and is identified as SEQ ID NO 6.

TABLE 6

| The marked ID of primer compound | Sequence Length (bp) | Sequence |
| --- | --- | --- |
| L3-18 | 2477 | ctggggacttcatgcgggagatacaatgacaaccgatattccgactgt |
| | | tttcactttagccggaaatatatcttttgatattaaagatgagtctgg |
| | | tgaggtaattggatctgctgttgcttcgaaagatactagaaagatagt |
| | | cattacttttcacagcacggagcagacctctcaaacacagggaaaat |
| | | tgacggggccttctcaatttttttacattgggatgttgaacaggtttc |
| | | tcgagttgtgggcgtaagaataattgcactgtcagtggtcaaaagttt |
| | | acttgagaggagggtaaaaatgtgacgaggatgacagctaaagtggcg |
| | | agaactgggcatttgttcgcggtcttattgattttgatgagtatgtta |
| | | acaggcttagtgacaagtggcagttcagttgtgacagccactgctaac |
| | | attcgcccaacctataaaaccaatgctaatggtacctatccagaaaat |
| | | tcgtggcaggtcacgggacaacaaaatgtgatcaatcaacgcggcggg |
| | | gatcaagtttcagggtgggataacaatacaacatgggatggtgatgcg |
| | | actaataccacgaattcttacctgaaatttggtgacccaataatccg |
| | | gattatcagattcgaaaatatgctaaagagacgaataccccggattg |
| | | tacgacgtttatttgaacgtcaaaggcaatacacagcaaaatgtgaag |
| | | cctgtagatattgtcttagttgttgatatgtctgggtcaatggagttc |
| | | aacagatataacacgaatcgagccggtgctgttcgtacaggtgttaag |
| | | aatttcttgacatctattcaaaacgccggtctgggtaattacgtcaat |
| | | gttggtttaattgggttttctagtcctggttatatcggtggcgaatcg |
| | | ggttatattagtgtcaaattaggcaaagcaggtaatgccagccagcaa |
| | | caagcgattaatggtgcattgaatccaaggtttcaaggggtacgtat |
| | | acgcagattggtttgcggcaaggatcagccatgctgaatgcggacacc |
| | | agtggcaataaaaaaatgatgattttgttaactgatggacgtgccgac |
| | | tttttctaacaaggtgataaattcagagtggataaatggcacattgta |
| | | tggcactaattttggatccagaagagatgaacccagcgataccgcaca |
| | | acttcgatggccgtacaccgatagttcaggtaataccatatatgatac |
| | | ttggcccgcaacattaggtgaggctaagaatgcaaaagatagcggtaa |
| | | tgaggtgcacgctttaggcattcaactggctgacgaccgccaatacat |
| | | gacaaaagaaaaaatacgccaaaacatgcaacttattaccaattcacc |
| | | ggatttatacgaagatgctgatagtgccgacgctgttgaggcttattt |
| | | gaacaatcaggcaaaggatattatcaaaaattttaatactgtcaccga |

TABLE 6-continued

| The marked ID of primer compound | Sequence Length (bp) | Sequence |
|---|---|---|
| | | tggcacgatcacagacccgattggtacgcaatttcaatatgcaaacaa |
| | | ccaggcgaccgttacgagtgtcggcaagcaaactgtgccagcaagtga |
| | | gttgccaagtgcggcgatccaagatggtcaattgacggtgaatcacat |
| | | gaacttgggtcaggatcaggaagttcaaatccattatcaagtacggat |
| | | caaaacagaggatgctggcttcaagcctgattttggtaccaaatgaa |
| | | tggtgaaacattgttgacaccaaaagcgggcgctgccgctgttgactt |
| | | tgggattccttcaggcagggcaccagcaactacagtttatgtgcagaa |
| | | gcaatggcgccagttaagcaatcaatcgttaccggatacgctcaacgt |
| | | cacggtgcagcgaaaagtggctgacggttcgcttgatccaaattggca |
| | | acagaccttagtccttaaaaaagctgataactggaaagctagctttac |
| | | ggcacctgcgtataacaatcagggtcaaagttttcatatgtcgttaa |
| | | gagtgaagatgcctcgggaattgatttgagttcgtttatcagttctca |
| | | aaatatggatcagcaaacagcaacgttgactttgacaaatcagcagta |
| | | tggttttcaatttcagaaaaaaacaaccgatggtactgatttatcagc |
| | | agatcagttgaaggccatgcagtttaacttaacccagtacagcgataa |
| | | cagttttcagcaggtatccaaaaccaacgccatcacgtcaacggatct |
| | | gcaggcactagcgccggggtattacggtattcaggaagctgcagcacc |
| | | tacaggttatcaacttgatgggacaatgtatcttttcagctaacgtc |
| | | tgatgggcaatggcaataccatggcacaaaggacaatgtgacatcagg |
| | | gagtgttattaatggccagcagactttgaatcctgttggtgataagtc |
| | | agatgattttacggtgaccgggtagatct |

Figure 4:
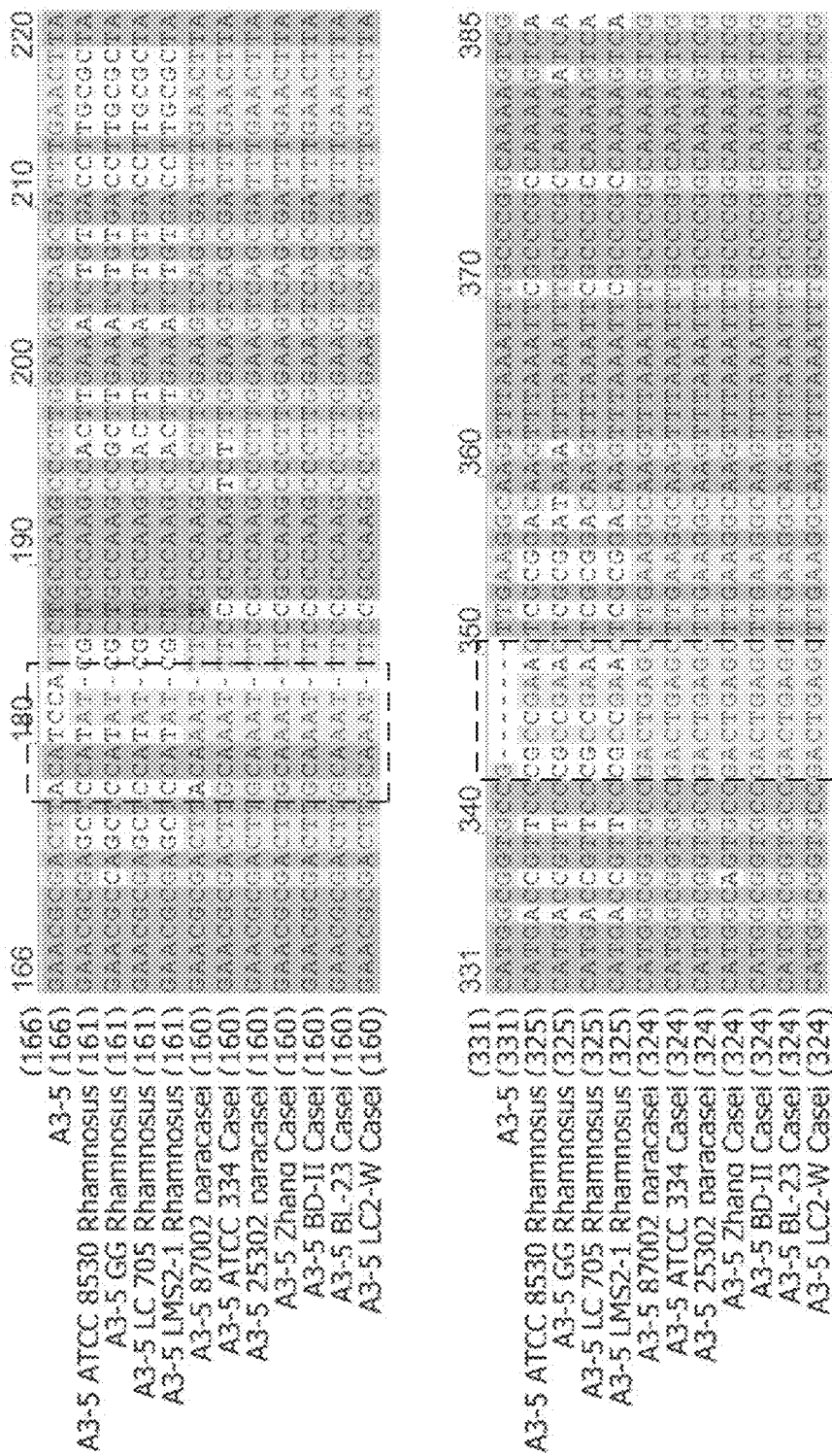
FIG. 4 is a comparing RAPD genetic variation map of A3-5.
Figure 5:
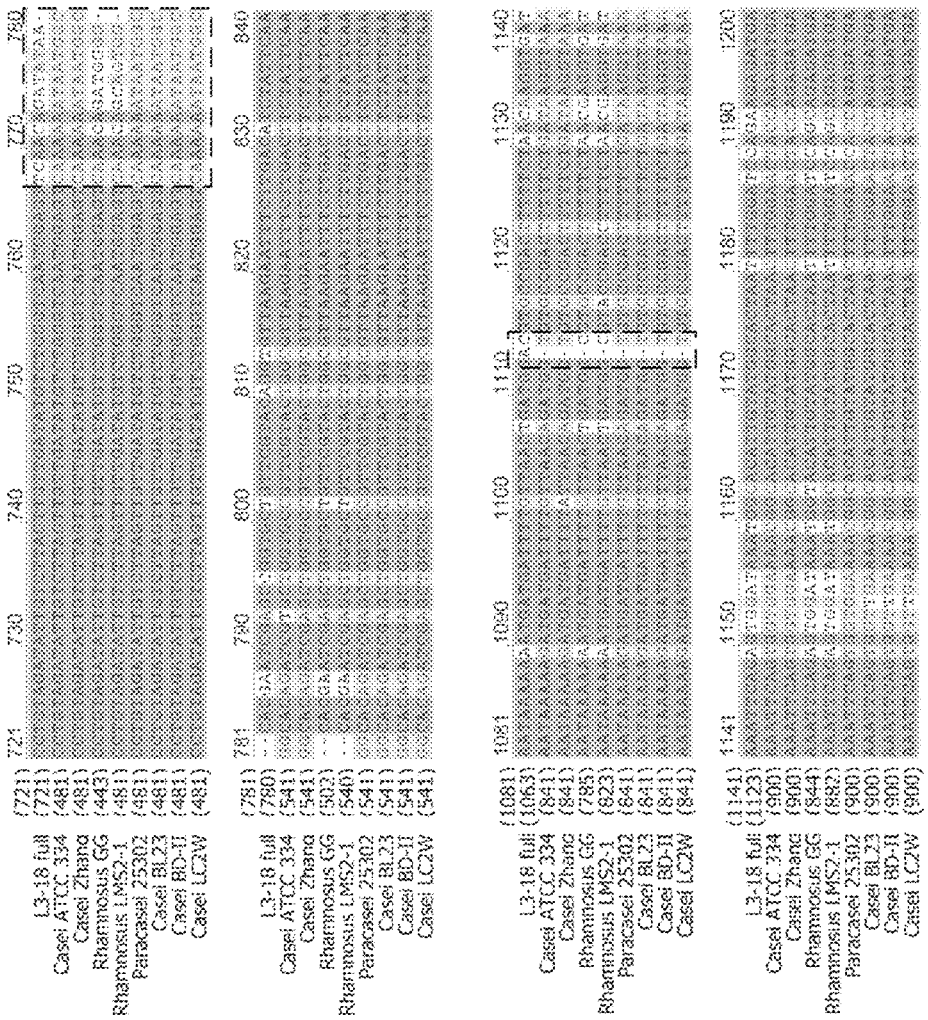
FIG. 5 is a comparing RAPD genetic variation map of L3-18.

Through above-presented experiment results of PCR and RAPD, it is able to initially know that the A3-5 and L3-18 may include the unique sequence fragments of the *Lactobacillus paracasei* subsp. *paracasei* NTU 101. Therefore, in order to further confirm whether the A3-5 and L3-18 does include the unique sequence fragments, the homologous DNA sequence data from Genbank are used to make a sequence comparison with the A3-5 and L3-18. Please refer to FIG. 4 and FIG. 5, there are shown comparing RAPD genetic variation maps of the A3-5 and L3-18. After comparing with the homologous DNA sequence, the rectangle dashed line encloses a unique sequence fragment of A3-5 in FIG. 4, and this unique sequence fragment in A3-5 can be used for carrying out the strain (mutant) identification of the NTU 101 by using the DNA molecular marker technology. Moreover, the rectangle dashed line also encloses a unique sequence fragment of L3-18 in FIG. 5, and this unique sequence fragment in L3-18 can also be used for carrying out the strain (mutant) identification of the NTU 101 by using the DNA molecular marker technology. FIG. 4 and FIG. 5 are generated by NCBI BLAST search of A3-5 and L3-18 sequences against complete genome sequences of *Lactobacillus casei* group species. The genome sequences used in FIG. 4 and FIG. 5 includes *Lactobacillus casei* ATCC 334 (GenBank accession/version no. NC_008526.1), *L. casei* str. Zhang (accession/version no. NZ_CP001084.1), *L. casei* BDII (accession/version no. NC_017474.1), *L. casei* LC2W (accession/version no. NC_017473.1), *L. paracasei* subsp. *paracasei* 87002 (accession/version no. NC_002112.1), *L. paracasei* subsp. *paracasei* 25302 (accession/version no. NZ_ACGY00000000.1), *L. rhamnosus* GG (accession/version no. NC_013198.1), *L. rhamnosus* LMS2-1 (accession/version no. NZ_ACIZ00000000.1), *L. rhamnosus* ATCC8530 (accession/version no. NC_017491.1) and *L. rhamnosus* Lc 705 (accession no. NC_013199.1). The alignments of A3-5 and L3-18 RAPD marker which derived from PCR amplification of *L. paracasei* subsp. *paracasei* NTU 101 genome showed that both RAPD markers contains unique DNA sequence that distinguish itself to the conserved counterpart of other *Lactobacillus casei* group species (in silico).

Because both the A3-5 and L3-18 include the unique sequence fragment for identifying the NTU 101, it needs to further check the specificity of the DNA molecular marker of the A3-5 and L3-18. As shown in following table 7, which records and lists a plurality of primers for checking the specificity of the DNA molecular marker of the A3-5 and L3-18. In which, primers 18FF, 18FR, L3-18F, L3-18R, L3-18F2, L3-18R2, L3-18F3, A3-5F, A3-5R, A3-5F2, A3-5R2, A3-5F3, A3-5R3, A3-5F4, A3-5R4, A3-5F5, A3-5R6, A3-5F6, and A3-5R7 are respectively identified as SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45.

TABLE 7

| Target | Primer ID | Sequence (5'→3') |
|---|---|---|
| L3-18 | 18FF | ATGCGGGAGATACAATGACAACCG |
|  | 18FR | CCCGTCAATTTTCCCTGTGTTTGA |
|  | L3-18F | GAAAATTGACGGGGCCTTCTCA |
|  | L3-18R | ACTGACAGTGCAATTATTCTTACGCCC |
|  | L3-18F2 | AAAACCAATGCTAATGGTACCTATCCAG |
|  | L3-18R2 | GGGGTCACCAAATTTCAGGTAAGAAT |
|  | L3-18F3 | GTCTGGGTCAATGGAGTTCAACAGATATA |
| A3-5 | A3-5F | GGCATGGCGGTGCCGTTGAA |
|  | A3-5R | ATCCCCGAATGGTGCCAGCA |
|  | A3-5F2 | GCCGAACGCGACTTACATCCA |
|  | A3-5R2 | GGCAATTTAAACTTGCCTTCAACGG |
|  | A3-5F3 | CGCCGAACGCGACTTACATC |
|  | A3-5R3 | GGCAAATTTAAACTTGCCTTCAACG |
|  | A3-5F4 | GCGACTTACATCCATTCTGCCAAG |
|  | A3-5R4 | GAAATTTAAACTTGCCTTCAACGGCA |
|  | A3-5F5 | GCCGAACGCGACTTAGATCCATT |
|  | A3-5R5 | TAAACTTGCCTTCAACGGCACCG |
|  | A3-5F6 | GCCGAACGCGACTTACAGCCA |
|  | A3-5R7 | TTTAAACTTGCCTTCAACGGCAC |

Figure 6A:
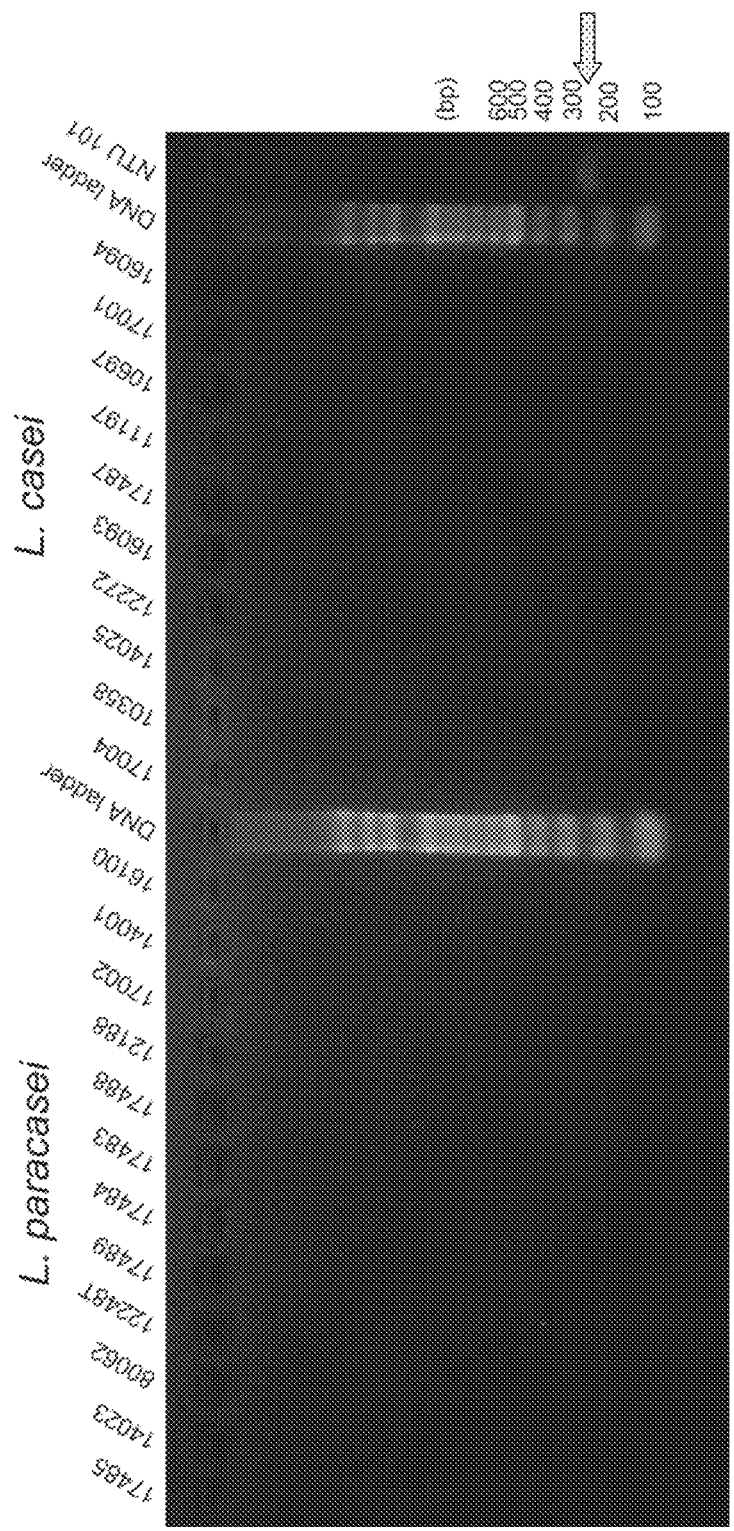
FIG. 6A and FIG. 6B are specificity test diagrams of the RAPD genetic variation map of A3-5.
Figure 6B:
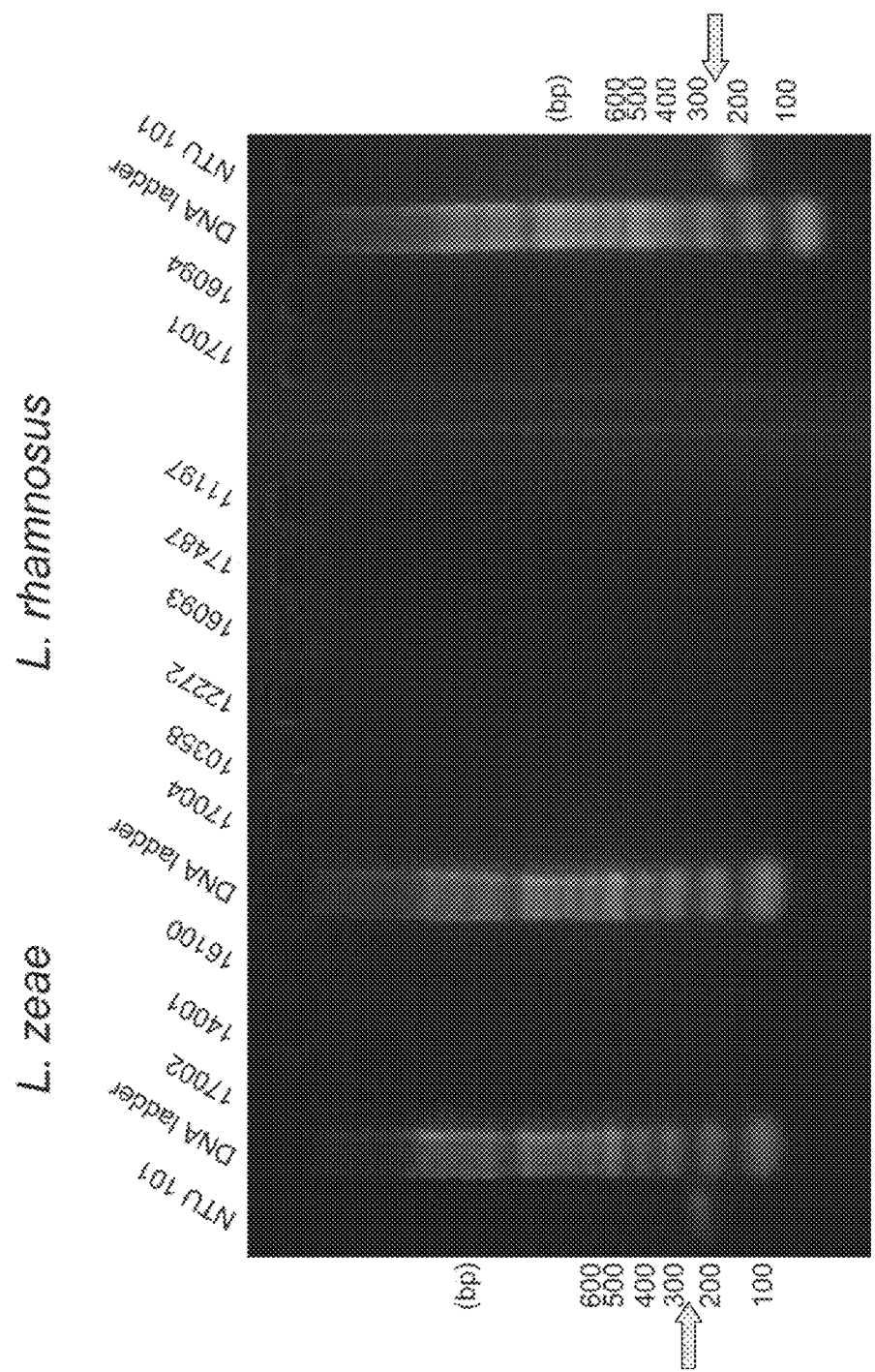

Please refer to FIG. 6A and FIG. 6B, there are shown specificity test diagram of the RAPD genetic variation map of A3-5. As shown in FIG. 6A and FIG. 6B, after completing the specificity test by using the primers listed in table 7, it is able to find that the A3-5 (F3/R3) indeed includes the specificity of NTU 101, so that the nucleotide sequence of the A3-5 can be used for carrying out the strain (mutant) specificity of the *Lactobacillus paracasei* subsp. *paracasei* NTU 101 proposed by the present invention. Moreover, as shown in Sequence Listing, the primer compound A3-5F3 is identified as SEQ ID NO 4 and includes the sequence length of 20 bp; besides, the primer compound A3-5R3 is identified as SEQ ID NO 5 and includes the sequence length of 25 bp.

Thus, through the descriptions, the *lactobacillus* mutant of *Lactobacillus paracasei* subsp. *paracasei* NTU 101, the nucleotide sequence for NTU 101, and the primers for nucleotide sequence of NTU 101 of the present invention has been completely introduced and disclosed; in summary, the present invention has the following advantages:

In the present invention, the nucleotide sequence for *Lactobacillus* NTU 101 and the primers for the nucleotide sequence are proposed in order to facilitate the person skilled in *Lactobacillus* filed capable of carrying out the strain (mutant) identification of the *Lactobacillus* NTU 101 according to the present invention. Moreover, the person skilled in *Lactobacillus* filed can also rapidly complete the strain (mutant) identification of the *Lactobacillus* NTU 101 by using DNA molecular marker technology, without culturing any isolated *Lactobacillus* strain or live *Lactobacillus* bacteria.

Next, following paragraphs will introduce the health applications of the *Lactobacillus paracasei* subsp. *paracasei* NTU 101. The *Lactobacillus paracasei* subsp. *paracasei* NTU 101 can be further made into a pure *lactobacillus* powder or a complex *lactobacillus* powder, and an specific intake dosage of the pure *lactobacillus* powder or the complex *lactobacillus* powder for an adult user used to reduce gastric mucosal lesion area and lesion index as well as histamine concentration in gastric mucosal is at least 4 g. In order to prove the aforesaid health functionalities of the pure *lactobacillus* powder or the complex *lactobacillus* powder made from the *Lactobacillus paracasei* subsp. *paracasei* NTU 101, a variety of experiments have been carried out.

8-week old SD (Sprague-Dawley) rats with the weight of 250 g-275 g are chosen to be the experimental animals. These SD rats are divided into Control (C) group, 0.5-fold (0.5×) group, 1-fold (1×) group, 5-fold (5×) group, live bacteria (Live) group, dead bacteria A (D-A) group, and dead bacteria B (D-B) group, wherein each of the divided groups consist of 8 SD rats. By using the BSA (Body Surface Area) formula provided by FDA (Food and Drug Administration), a fundamental dosage for the testing samples used in this experiment is calculated to be 0.3 $gkg^{-1}day^{-1}$ according to the specific intake dosage of an adult. Therefore, all rat groups and testing sample dosages are integrated in following table 8.

TABLE 8

| Group | Testing Smaple | dosage (g/kg rat bw) | including bacterial count |
|---|---|---|---|
| C | Reverse Osmosis Water |  |  |
| 0.5X | complex *lactobacillus* powder | 0.15 | $3 \times 10^9$ CFU/g |
| 1.0X | complex *lactobacillus* powder | 0.3 | $3 \times 10^9$ CFU/g |
| 5.0X | complex *lactobacillus* powder | 1.5 | $3 \times 10^9$ CFU/g |
| Live | pure *lactobacillus* powder | 0.3 | $3 \times 10^{11}$ CFU/g |
| D-A | pure *lactobacillus* powder | 0.3 | $3 \times 10^{11}$ cells/g |
| D-B | pure *lactobacillus* powder | 0.3 | $3 \times 10^{12}$ cells/g |

During 8-week experimental period, the experimental SD rats are daily fed with chow diet and administrated with the corresponding testing samples, wherein the testing samples are solved in 1.0 mL sterilized distilled water and then administrated to the SD rats by using a sterilized plastic syringe having stainless steel feeding needle.

According to following table 9, the weight of the SD rats in the groups rises with the experiment time passes; moreover, the SD rats in each of the groups have no obvious weight-variation difference.

TABLE 9

| Group | Week 2 | Week 4 | Week 6 | Week 8 |
|---|---|---|---|---|
| C | 357.84 ± 18.55 | 424.31 ± 25.04 | 464.13 ± 27.39 | 508.03 ± 30.65 |
| 0.5X | 359.31 ± 12.92 | 427.80 ± 13.70 | 468.78 ± 12.06 | 523.54 ± 14.14 |
| 1X | 364.43 ± 12.24 | 434.34 ± 18.27 | 463.68 ± 18.22 | 517.61 ± 24.64 |
| 5X | 368.00 ± 8.55 | 434.86 ± 15.18 | 473.83 ± 13.41 | 522.70 ± 19.35 |
| Live | 352.89 ± 4.66 | 418.33 ± 10.32 | 459.41 ± 12.47 | 509.69 ± 17.06 |
| D-A | 363.11 ± 9.41 | 434.93 ± 12.76 | 474.33 ± 15.12 | 531.58 ± 22.58 |
| D-B | 365.23 ± 19.19 | 434.36 ± 29.51 | 477.61 ± 29.71 | 532.68 ± 35.14 |

Moreover, According to following table 10, it can find that, the fecal dry weight of the SD rats in all experimental group is obviously greater than the fecal dry weight of the SD rats in control group after continuously feeding the testing samples to all SD rats. Thus, the experiment data of table 10 proves that, long-term intake of the complex *lactobacillus* powder, the pure (live) *lactobacillus* powder, or the dead *lactobacillus* powder would effectively increase the fecal dry weight of animals.

TABLE 10

| Group | Week 2 | Week 6 | Week 8 |
|---|---|---|---|
| C | 8.27 ± 0.72bc | 5.17 ± 0.41a | 4.61 ± 0.69a |
| 0.5X | 8.54 ± 0.34cd | 5.71 ± 0.34bc | 5.61 ± 0.31bc |
| 1X | 8.65 ± 0.40cd | 5.95 ± 0.32cd | 5.94 ± 0.24c |
| 5X | 8.97 ± 0.37d | 5.60 ± 0.25bc | 5.63 ± 0.25bc |
| Live | 8.67 ± 0.40cd | 5.55 ± 0.44b | 5.85 ± 0.24c |

TABLE 10-continued

| Group | Week 2 | Week 6 | Week 8 |
|---|---|---|---|
| D-A | 8.98 ± 0.68d | 6.23 ± 0.37d | 6.01 ± 0.43c |
| D-B | 8.35 ± 0.58bc | 5.85 ± 0.26bc | 5.70 ± 0.18bc |

Subsequently referring to following table 11, which records the statistics counts of the *C. perfringens* contained by the fecal and cecum of the SD rats. Comparing to control group, the *C. perfringens* amount in the fecal of the SD rats in all experimental groups is obviously lower after continuously feeding the testing samples to the SD rats for 4 weeks and 6 weeks. Moreover, table 11 also reveals that the continuously 8-week feeding of the testing samples would significantly reduce the count of the *C. perfringens* in the fecal of the SD rats in all experimental groups. Similarly, after completing the continuously 8-week feeding of the testing samples, the count of the *C. perfringens* in the cecum of the SD rats in all experimental groups would be obviously reduced.

TABLE 11

| | *C. perfringens* count in fecal (CFU/g) | | | *C. perfringens* count in cecum (CFU/g) |
|---|---|---|---|---|
| Group | 4-Week | 6-Week | 8-Week | 8-Week |
| C | 0.21 ± 0.47b | 2.17 ± 2.89c | 4.96 ± 2.77d | 5.42 ± 5.07c |
| 0.5X | 0.00 ± 0.00a | 0.00 ± 0.00a | 1.00 ± 1.46a | 0.21 ± 0.59b |
| 1X | 0.00 ± 0.00a | 0.00 ± 0.00a | 0.38 ± 0.58a | 0.00 ± 0.00a |
| 5X | 0.00 ± 0.00a | 0.00 ± 0.00a | 0.83 ± 0.99a | 0.13 ± 0.35b |
| Live | 0.00 ± 0.00a | 0.00 ± 0.00a | 1.29 ± 1.46ab | 0.00 ± 0.00a |
| D-A | 0.00 ± 0.00a | 0.00 ± 0.00a | 2.75 ± 2.13bc | 0.00 ± 0.00a |
| D-B | 0.00 ± 0.00a | 0.00 ± 0.00a | 3.00 ± 1.99c | 0.04 ± 0.12a |

Next referring to following table 12, which records the statistics counts of the *Bifidobacterium* spp. contained by the fecal and cecum of the SD rats. Comparing to control group, the *Bifidobacterium* spp. amount in the fecal of the SD rats in all experimental groups is obviously higher after continuously feeding the testing samples to the SD rats for 4 weeks and 6 weeks. Moreover, table 12 also reveals that the continuously 8-week feeding of the testing samples would significantly enhance the count of the *Bifidobacterium* spp. in the fecal of the SD rats in all experimental groups. Similarly, after completing the continuously 8-week feeding of the testing samples, the count of the *Bifidobacterium* spp. in the cecum of the SD rats in all experimental groups would be obviously increased.

TABLE 12

| | *Bifidobacterium* spp. count in fecal (CFU/g) | | | *Bifidobacterium* spp. count in fecal (CFU/g) |
|---|---|---|---|---|
| Group | 4-Week | 6-Week | 8-Week | 8-Week |
| C | 4.40 ± 0.29a | 4.54 ± 0.31a | 4.76 ± 0.34a | 4.47 ± 0.49a |
| 0.5X | 4.93 ± 0.30c | 5.68 ± 0.20b | 5.98 ± 0.27cd | 6.53 ± 0.57d |
| 1X | 5.10 ± 0.29c | 5.57 ± 0.40b | 6.05 ± 0.2cd | 6.76 ± 0.36de |
| 5X | 5.03 ± 0.19c | 5.54 ± 0.24b | 6.33 ± 0.58d | 7.10 ± 0.43e |
| Live | 8.56 ± 0.42d | 8.59 ± 0.28c | 8.72 ± 0.33e | 9.03 ± 0.30f |
| D-A | 4.82 ± 0.38bc | 5.58 ± 0.62b | 5.89 ± 0.46c | 5.88 ± 0.16c |
| D-B | 4.87 ± 0.29bc | 5.29 ± 0.6ab | 6.15 ± 0.35cd | 5.56 ± 0.34c |

Continuously, please refer to following table 13, which records the statistics counts of the *Lactobacillus* spp. contained by the fecal and cecum of the SD rats. Comparing to control group, the *Lactobacillus* spp. amount in the fecal of the SD rats in all experimental groups is obviously higher after continuously feeding the testing samples to the SD rats for 4 weeks and 6 weeks. Moreover, table 13 also reveals that the continuously 8-week feeding of the testing samples would significantly enhance the count of the *Lactobacillus* spp. in the fecal of the SD rats in all experimental groups. Similarly, after completing the continuously 8-week feeding of the testing samples, the count of the *Lactobacillus* spp. in the cecum of the SD rats in all experimental groups would be obviously increased.

TABLE 13

| | *Lactobacillus* count in fecal (CFU/g) | | | *Lactobacillus* count in fecal (CFU/g) |
|---|---|---|---|---|
| Group | 4-Week | 6-Week | 8-Week | 8-Week |
| C | 7.40 ± 0.16a | 8.70 ± 0.32a | 9.09 ± 0.16a | 8.15 ± 0.39a |
| 0.5X | 8.06 ± 0.14b | 8.81 ± 0.20ab | 9.39 ± 0.23b | 8.82 ± 0.16bc |
| 1X | 8.07 ± 0.04b | 8.92 ± 0.17bc | 9.64 ± 0.28b | 8.96 ± 0.15bc |
| 5X | 8.04 ± 0.14b | 8.80 ± 0.14ab | 9.41 ± 0.17b | 8.77 ± 0.23bc |
| Live | 8.29 ± 0.32c | 9.11 ± 0.19cd | 9.62 ± 0.25b | 9.51 ± 0.31d |
| D-A | 8.08 ± 0.19b | 9.02 ± 0.16bcd | 9.46 ± 0.15b | 8.91 ± 0.24bc |
| D-B | 8.06 ± 0.18b | 9.15 ± 0.14d | 9.44 ± 0.17b | 8.71 ± 0.28bc |

Next referring to below table 14, which records the short-chain fatty acids (SCFAs) concentrations contained by the cecum of the SD rats. Comparing to control group, the SCFAs concentrations (including acetic acid, propionic acid and butyric acid concentrations) in the cecum of the SD rats in all experimental groups is obviously higher after continuously feeding the testing samples to the SD rats for 8 weeks, except for the SD rats in the D-B group. It is well known that, these short-chain fatty acids, especially the acetic acid, are able to lower the pH value of intestine and inhibit the growth of saprophytes in the intestine.

TABLE 14

| Group | acetic acid (mM) | propionic acid (mM) | butyric acid (mM) |
|---|---|---|---|
| C | 25.06 ± 2.94ab | 8.80 ± 0.85a | 5.78 ± 1.69a |
| 0.5X | 36.34 ± 5.04c | 19.97 ± 2.13de | 6.93 ± 0.57a |
| 1X | 45.07 ± 3.78d | 18.84 ± 1.66d | 17.78 ± 4.79c |
| 5X | 46.62 ± 3.00d | 22.69 ± 2.71f | 17.95 ± 3.98c |
| Live | 45.19 ± 2.01d | 21.35 ± 1.02ef | 14.79 ± 1.35b |
| D-A | 27.41 ± 4.60b | 10.53 ± 1.29b | 6.63 ± 1.39a |
| D-B | 23.39 ± 4.79a | 14.51 ± 2.22c | 13.26 ± 2.89b |

Figure 7:
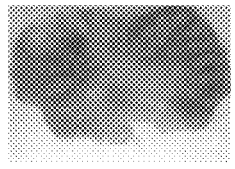
FIG. 7 shows gastric wall images.
Figure 7:
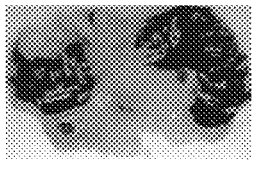
Figure 7:
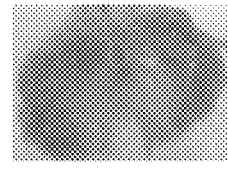
Figure 7:
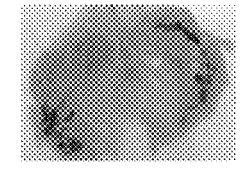
Figure 7:
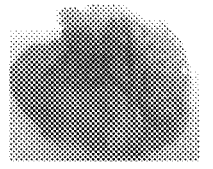
Figure 7:
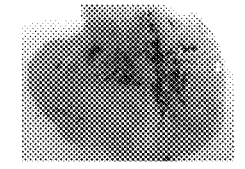
Figure 7:
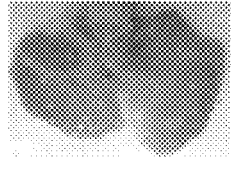
Figure 7:
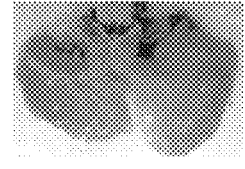
Figure 7:
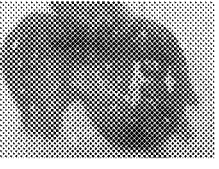
Figure 7:
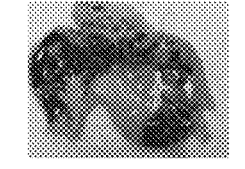
Figure 7:
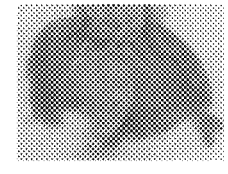
Figure 7:
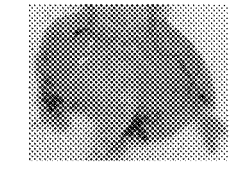
Figure 7:
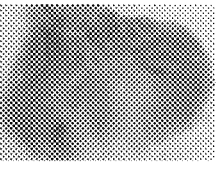
Figure 7:
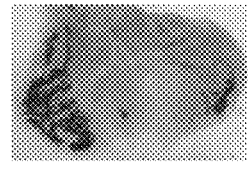

Subsequently referring to following table 15, which records the statistics gastric lesion data of the SD rats; moreover, please simultaneously refer to the gastric wall images shown by FIG. 7. From FIG. 7 and table 15, it can find that the lesion area and the lesion index of the SD rats in C group are 4.11 mm$^2$ and 0.0635, respectively. However, after continuously feeding the testing samples to the SD rats in the experimental groups, the lesion index reducing percent of the SD rats in the experimental groups respectively reaches to 98.74%, 67.71% and 76.96 comparing with the C group. Moreover, the pH value of gastric acid, the total gastric acidity and the volume of gastric acid between the SD rat in the experimental groups and the SD rat in the control group shows no obvious discrepancy. Therefore, the experiment data of FIG. 7 and table 15 prove that, long-term intake of the complex *lactobacillus* powder, the pure (live) *lactobacillus* powder, or the dead *lactobacillus* powder would effectively reduce animal's gastric mucosal lesion area and lesion index.

TABLE 15

| Group | Lesion area (mm²) | Total mucosal area (mm²) | Lesion index | Volume of gastric acid (mL) | PH value of gastric acid | Total gastric acidity (mEq/L) |
|---|---|---|---|---|---|---|
| C | 4.11 ± 2.14c | 677.16 ± 92.39abc | 0.0635 ± 0.0419c | 5.00 ± 1.82a | 1.77 ± 0.43a | 73.11 ± 15.60ab |
| 0.5X | 0.37 ± 0.29ab | 780.33 ± 171.63bc | 0.0047 ± 0.0037ab | 5.23 ± 1.66a | 1.82 ± 0.65a | 78.69 ± 22.71ab |
| 1X | 0.47 ± 0.44ab | 792.31 ± 162.64c | 0.0061 ± 0.0060ab | 5.10 ± 2.34a | 1.76 ± 0.34a | 86.28 ± 18.36b |
| 5X | 0.07 ± 0.10a | 713.48 ± 94.02abc | 0.0010 ± 0.0013a | 5.58 ± 2.66a | 1.55 ± 0.32a | 77.68 ± 11.50ab |
| Live | 0.06 ± 0.06a | 711.03 ± 100.71abc | 0.0008 ± 0.0009a | 6.24 ± 1.43a | 1.56 ± 0.38a | 78.99 ± 15.18ab |
| D-A | 1.36 ± 0.97b | 652.91 ± 54.00ab | 0.0205 ± 0.0147b | 5.70 ± 1.77a | 1.69 ± 0.40a | 80.18 ± 15.95ab |
| D-B | 0.92 ± 0.87ab | 638.79 ± 82.88a | 0.0148 ± 0.0147ab | 5.58 ± 2.09a | 1.75 ± 0.30a | 68.74 ± 7.67a |

Furthermore, the following table 16 records the statistics lipid peroxide data of the SD rats. From table 16, it can find that the malonaldehyde (MDA) concentration in the gastric mucosal of the SD rats in C group is 23.28 µM. However, after continuously feeding the testing samples to the SD rats in the experimental groups, the MDA concentration in the gastric mucosal of the SD rats in the experimental groups are obviously reduced. Moreover, comparing the 1.69 U/mL superoxide dismutase (SOD) concentration in the gastric mucosal of the SD rats in C group, the SD rats in the experimental groups been fed with the test samples are determined to include higher SOD concentrations in the gastric mucosal thereof. Therefore, the experiment data of table 16 proves that, long-term intake of the complex *lactobacillus* powder, the pure (live) *lactobacillus* powder, or the dead *lactobacillus* powder would effectively reduce animal's gastric mucosal lesion.

TABLE 16

| Group | MDA conc. of stomach (µM) | SOD concentration (U/mL) | Histamine (µ/g) | PGE$_2$ (pg/mg protein) |
|---|---|---|---|---|
| C | 23.28 ± 3.75d | 1.69 ± 0.17b | 111.94 ± 2.78c | 1433.84 ± 45.03a |
| 0.5X | 16.96 ± 3.91b | 2.59 ± 0.20c | 67.24 ± 5.35a | 3078.21 ± 50.94d |
| 1X | 16.15 ± 2.22ab | 3.22 ± 0.62d | 69.18 ± 6.90a | 3128.64 ± 57.18bc |
| 5X | 13.46 ± 1.76a | 4.20 ± 0.39e | 74.07 ± 8.43a | 3208.15 ± 21.95b |
| Live | 14.90 ± 1.31ab | 4.29 ± 0.59e | 70.94 ± 12.9a | 3103.60 ± 94.39a |
| D-A | 14.90 ± 1.46ab | 4.07 ± 0.79e | 101.93 ± 3.46b | 3123.39 ± 46.25bc |
| D-B | 20.34 ± 2.48c | 3.36 ± 0.93d | 113.04 ± 4.88c | 3093.00 ± 78.65bc |

Besides, through the table 16, it can also find that, after continuously feeding the testing samples to the SD rats in the experimental groups, the histidine concentration in the gastric mucosal of the SD rats in the experimental groups are obviously reduced, and the Prostaglandin E2 (PGE$_2$) concentration are increased. Therefore, the experiment data of table 16 proves that, long-term intake of the complex *lactobacillus* powder, the pure (live) *lactobacillus* powder, or the dead *lactobacillus* powder would help to lower the histidine concentration and enhance the (PGE$_2$ concentration for animals.

The above description is made on embodiments of the present invention. However, the embodiments are not intended to limit scope of the present invention, and all equivalent implementations or alterations within the spirit of the present invention still fall within the scope of the present invention.

What is claimed is:

1. A probiotic composition containing *Lactobacillus paracasei* subsp. *paracasei* NTU 101 for ameliorating intestinal flora, reducing gastric mucosal lesion index, and decreasing histamine concentration in gastric mucosal, being a pure *lactobacillus* powder made of a *Lactobacillus* mutant;
   wherein the *Lactobacillus* mutant is a *Lactobacillus paracasei* subsp. *paracasei* NTU 101 having a nucleotide sequence of SEQ ID NO 1, and deposited with Deutsche Sammlung von Mikroorganismen and Zellkulturen GmbH (DSMZ) on Nov. 18, 2013;
   wherein the accession number of the *Lactobacillus paracasei* subsp. *paracasei* NTU 101 is DSM 28047;
   wherein the sequence length of the nucleotide sequence of SEQ ID NO 1 is 838 bp, and the nucleotide sequence of SEQ ID NO 1 is able to be identified by using a plurality of specific primers selected from the group consisting of: (1): A3-5F3 CGCCGAACGCGACTTA-CATC (SEQ ID NO 4) and (2): A3-5R3 GGCAAATT-TAAACTTGCCTTCAACG (SEQ ID NO 5); moreover, the aforesaid specific primers further comprising a first nucleotide sequence of SEQ ID NO 2 and a second nucleotide sequence of SEQ ID NO 3;
   wherein after administrating the pure *lactobacillus* powder by 4 g/day for 8 weeks, the count of *Clostridium perfringens* and *Bifidobacterium* spp. in human cecum would be respectively reduced and increase, so as to ameliorate intestinal flora; moreover, the gastric mucosal lesion index being simultaneously decreased by 98.74%, and the histidine concentration in human gastric mucosal being also reduced;
   wherein the viable count of the *Lactobacillus paracasei* subsp. *paracasei* NTU 101 in the pure *lactobacillus* powder is ranged from $3\times10^9$ CFU/g to $1\times10^{11}$ CFU/g.

2. The probiotic composition containing *Lactobacillus paracasei* subsp. *paracasei* NTU 101 of claim 1, wherein the nucleotide sequence of the *Lactobacillus paracasei* subsp. *paracasei* NTU 101 can be formed by treating the RAPD (Random Amplification of Polymorphic DNA) and the PCR (Polymerase Chain Reaction) process to the specific primers.

3. The probiotic composition containing *Lactobacillus paracasei* subsp. *paracasei* NTU 101 of claim 1, wherein when the *Lactobacillus paracasei* subsp. *paracasei* NTU 101 would produce lactic acid after being cultured in a culture medium containing at least one specific carbon source for at least 24 hours.

4. The probiotic composition containing *Lactobacillus paracasei* subsp. *paracasei* NTU 101 of claim 1, wherein when the *Lactobacillus paracasei* subsp. *paracasei* NTU 101 would produce lactic acid after being cultured in a culture medium containing at least one specific nitrogen source for at least 24 hours.

5. The probiotic composition containing *Lactobacillus paracasei* subsp. *paracasei* NTU 101 of claim 3, wherein the specific carbon source is selected from the group consisting of: Glucose, Galactose, D-ribose, Xylose, Fructose, α-Lactose, Maltose, Sucrose, Trehalose, Raffinose, myo-Inositol, Sorbitol, D-mannitol, Citric acid, Dextrin, Starch, and Molasses.

6. The probiotic composition containing *Lactobacillus paracasei* subsp. *paracasei* NTU 101 of claim 4, wherein the specific nitrogen source is selected from the group consisting of: Yeast extract, Beef extract, Peptone, Soytone, Tryptose, Corn-steep liquor, Casein, Urea, Ammonium citrate, and Ammonium sulfate.

* * * * *

SEQUENCE LISTING

<160> NUMBER OF SEQ ID NOS: 5

<210> SEQ ID NO 1
<211> LENGTH: 838
<212> TYPE: DNA
<213> ORGANISM: Lactobacillus mutant
<220> FEATURE:

<400> SEQUENCE: 1

```
agatctagcg ccattggtct tgaaagctcg cctgttgctg cagcattggc              50
aggattgcgc gcaaatgaag cgcgttacat ctggaataag tataaggaac             100
cttatatcac ttatccggct gccgaaaaac ctgacagtct cgcatgggtt             150
```

```
aatgaaattc tcgccgaacg cgacttacat ccattctgcc aagcccttgg            200
aagtcagcga tttgaactta ccggatttgc actgggttga ggtttactat            250
caagacggat tagccatcaa cgtgatgtat agcttgtccg accccaaaaa            300
acgcgcggtt ggctttaaac ttagcgatgg catggcggtg ccgttgaagg            350
caagtttaaa tttgcccggc aaaagtcgaa gcttgctggc accattcggg            400
gatctttttt cgtcatcaag gtcagccatt gaaaaaagac aacttttaa             450 cttgataagc ttacacatac aaaaaacggc cacggtgatg ttcctcaata            500
ttggaggtat gacatcaccg tggccatttt tgcgtataat cgtttaaaca            550
aagactgaaa tggccagctg aatatttaga acggtgatca cacccgtcag            600
aaaatagccg acccaccgca cgagttgcga attaacgtgg atacccatca            650
aatcacgccg attcgtcaag gccaccaacg ggaaaagcgt aaatggcaag            700
gcaatgctca atgacacctg cgcatagaca ataacttgct caaagttgtg            750
ttcgctaaaa ccgatcatga agccaatcac catgatggga atgagcgtca            800
caagtcgcgt cagcaacctc cgctcccaca atggcgct                         838

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 2
gtttctctcc                                                         10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 3
agcgccattg                                                         10

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 4
cgccgaacgc gacttacatc                                              20

<210> SEQ ID NO 5
<211> LENGTH: 25
<212> TYPE: DNA
<213> ORGANISM: Artificial Sequence
<220> FEATURE:
```

-continued

```
<223> OTHER INFORMATION: Description of Artificial Sequence: Synthetic
     oligonucleotides.

<400> SEQUENCE: 5
ggcaaattta aacttgcctt caacg                                          25
```